(12) United States Patent
Kyung et al.

(10) Patent No.: US 6,575,742 B2
(45) Date of Patent: Jun. 10, 2003

(54) OSTEOGENIC SUPPORT DEVICE FOR ORTHODONTIC TREATMENT

(76) Inventors: Hee Moon Kyung, Ulzi Apt. 101-803, 314-2 Beomeo 4 Dong, Susung Gu, Taegu (KR); Hyo Sang Park, 1-403 Shinsegae Town, 613 Bunji Susung 1 Ga, Susung Gu, Taegu (KR); Sung Min Bae, 101 Dong 1315 Ho Woobang Hangaram Town, 272-11 Bunji Susung 1 Ga, Susung Gu, Taegu (KR)

( * ) Notice: Subject to any disclaimer, the term of this patent is extended or adjusted under 35 U.S.C. 154(b) by 0 days.

(21) Appl. No.: 10/092,146

(22) Filed: Mar. 6, 2002

(65) Prior Publication Data

US 2002/0127510 A1 Sep. 12, 2002

(30) Foreign Application Priority Data

Mar. 7, 2001 (KR) ........................ 2001-6050 U

(51) Int. Cl.⁷ ............................. A61C 3/00; A61C 8/00
(52) U.S. Cl. .............................. 433/18; 433/173
(58) Field of Search ........................... 433/18, 173, 174

(56) References Cited

U.S. PATENT DOCUMENTS

| | | | | |
|---|---|---|---|---|
| 3,514,858 A | * | 6/1970 | Silverman | 433/171 |
| 5,921,774 A | * | 7/1999 | Kanomi et al. | 433/18 |
| 6,312,259 B1 | * | 11/2001 | Kvarnstrom et al. | 433/173 |
| 6,354,834 B2 | * | 3/2002 | Kanomi et al. | 433/18 |
| 2002/0182560 A1 | * | 12/2002 | Park et al. | 433/18 |

FOREIGN PATENT DOCUMENTS

KR 2020010006050 3/2001

* cited by examiner

Primary Examiner—Cary E. O'Connor
(74) Attorney, Agent, or Firm—Park & Sutton LLP; John K. Park

(57) ABSTRACT

An osteogenic support device for an orthodontic treatment comprises a platform, lower and upper projections extending downwardly and upwardly from the platform. The upper projection is substantially tapered from the platform toward a cap. The upper protection has a through opening substantially perpendicular to an axis of the lower projection. A first end of the elastic wire is hooked between the cap and the platform, and a second end of the elastic wire is hooked with an orthodontic wire which links each bracket attached on teeth of the orthodontic patient.

16 Claims, 5 Drawing Sheets

FIG. 3
FIG. 4
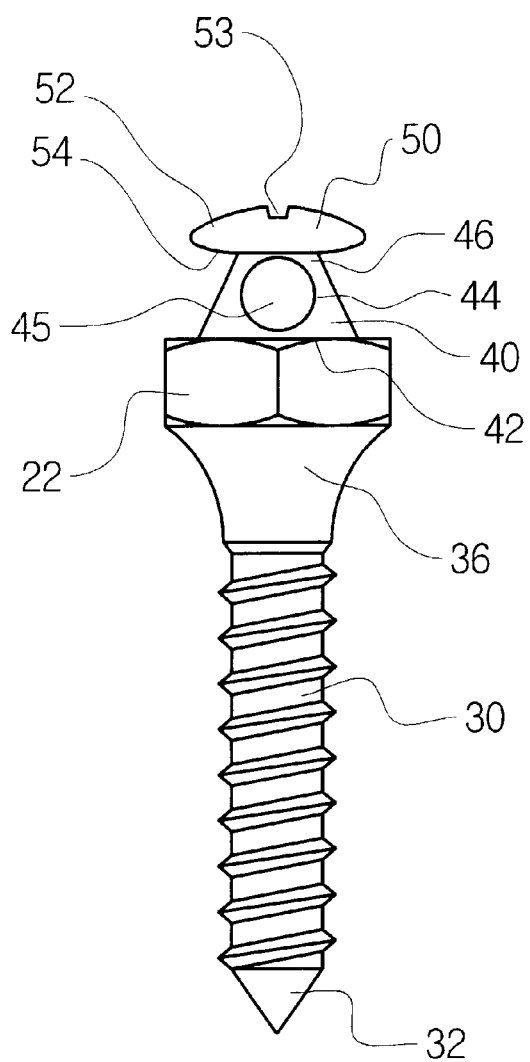
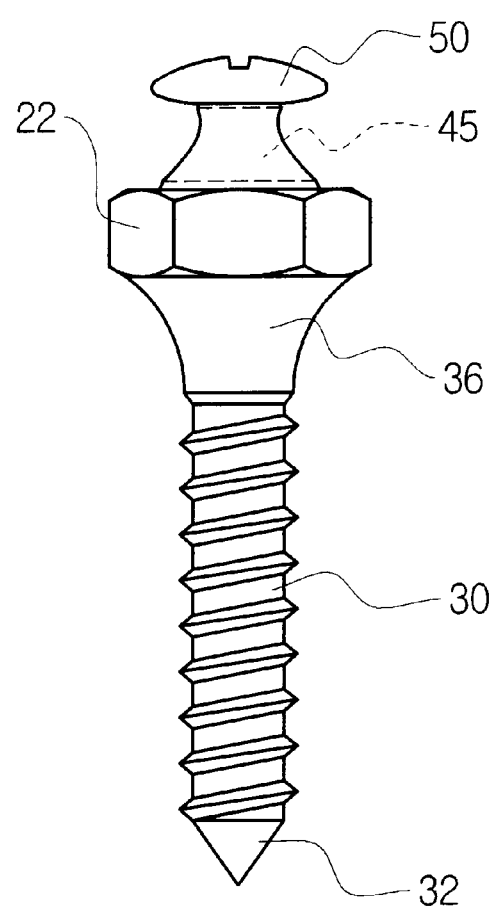

OSTEOGENIC SUPPORT DEVICE FOR ORTHODONTIC TREATMENT

CLAIMING FOREIGN PRIORITY

The applicant claims and requests a foreign priority, through the Paris Convention for the Protection of Industry Property, based on a patent application filed in the Republic of Korea (South Korea) with the filing date of Mar. 7, 2001, with the application number 20-2001-0006050, by the applicant. (See the Attached Declaration)

BACKGROUND OF THE INVENTION

The present invention relates to an orthodontic treatment device. More particularly, the invention relates to an osteogenic support device which serves to protect gum of an orthodontic patient while improving performance of an orthodontic treatment.

As a known method of orthodontic treatment, a jaw bone is used to provide an extra force to teeth of an orthodontic patient so as to efficiently realize a desired teeth rearrangement. Once brackets are glued on teeth in a required alignment, each of the glued teeth is connected using an orthodontic wire which serves to strain the teeth of an orthodontic patient. When an additional force is required for a desired teeth arrangement, a tiny piece of hygienic nailing device such as a hygienic screw is planted in a jaw bone structure of the orthodontic patient to provide an extra strain to the teeth. That is, an extra wire is hooked up both on an exposed side portion of the hygienic piece planted in the patient's jaw bone and on the base wire that retains each bracket on the teeth.

FIG. 10 shows a conventional osteogenic support device disclosed in Korean Utility Model No. 20-0183849 granted to the present inventors. As shown therein, the support device 100 includes a base platform 110, an upper projection 120 extending upwardly from the base platform 110, and a neck portion 130 extending downwardly from the base platform 110. A gum protect 140 and a screw portion 150 are sequentially formed from the neck portion 130. A cap 160 is formed on the upper projection 120 to allow a wire hookup on the upper projection 120. The screw portion 150 is pierced in a jaw bone of an orthodontic patient and the gum protect 140 serves to guard the gum of the orthodontic patient. However, the conventional osteogenic support device 100 allows a wire to move along the evenly formed outer periphery of the upper projection 120 thereby causing the wire to make an unwanted contact on the gum which may lead to gum inflammation and other side effects. In addition, the conventional support device 100 may easily lead to a delay in orthodontic treatment, because once the gum becomes inflamed, the orthodontic treatment has to halt until the gum recovers from the wire-related injury.

SUMMARY OF THE INVENTION

The present invention is contrived to overcome the conventional disadvantages and others. Accordingly, it is an object of the present invention to provide an osteogenic support device for an orthodontic treatment which minimizes a wire contact on the gum during the osteogenic orthodontic treatment. Another object is to improve efficiency in orthodontic treatment using an osteogenic jaw bone structure together with an elastic wire that links the support device and a regular wire worn on each bracket glued on teeth of an orthodontic patient.

To achieve the above-described objects, the osteogenic support device for an orthodontic treatment according to the present invention comprises a platform defined by a top side, a bottom side and an outer periphery. A lower projection having a pointed end extends from the bottom side of the platform so as to become pierced in an osteogenic jaw bone structure of an orthodontic patient for a limited time period.

An upper projection upwardly extends from the top side of the platform. The upper projection includes a base portion having a lower end, a mid portion, and an upper portion having an upper end. The lower end of the base portion of the upper projection is attached to the top side of the platform. The upper projection is substantially tapered from the base portion toward the upper portion thereof. In a preferred version, the mid portion of the upper protection has a through opening substantially perpendicular to an axis of the lower projection.

For a better performance, a cap is provided to include an upper surface and a lower surface. The upper end of the upper portion of the upper projection is attached to the lower surface of the cap. The lower surface of the cap is substantially larger in area than the upper end of the upper portion of the upper projection.

An elastic wire is provided to have first and second ends. The first end of the elastic wire is hooked between the cap and the platform. The second end of the elastic wire is hooked with an orthodontic wire which links each bracket attached on teeth of the orthodontic patient. Also, a gum protection between the platform and the lower projection is smoothly tapered from below the platform toward the lower projection and shaped in a truncated cone. The truncated cone shaped upper projection is between about 1.0 mm and about 3.0 mm in height. It is preferred that the lower projection is substantially threaded. The outer periphery of the platform is substantially surface-piled to facilitate manipulation of the support device. The upper surface of the cap is shaped in dome so the domed upper surface of the cap is partially depressed to form either a linear recess or a cross-shaped recess.

Advantages of the osteogenic support device for an orthodontic treatment according to the present invention are numerous in that: (1) the upper projection tapered toward the cap at least decreases or eliminates possibility that an elastic wire hooked over the cap by one end and the base wire linking each bracket glued on target by the other end may become in contact with gum, thereby preventing gum inflammation and other friction related gum diseases since the tapered upper projection serves to distance the elastic wire from the gum; (2) the tapered upper projection stabilizes placement of the elastic wire while preventing unwanted drooping and swaying of the elastic wire, thereby improving efficiency of the orthodontic treatment and decreasing an overall time period during which the lower projection stays pierced in the osteogenic jaw bone structure; and (3) the gum protection formed in taper from the platform toward the lower projection is provided such that it minimizes gum stimulation and gum contact area while staying contacted with the gum, thereby overcoming disadvantages by a conventional disk-typed gum contact that disregards pressure on the gum.

Although the present invention is briefly summarized, the fuller understanding of the invention can be obtained by the following drawings, detailed description and appended claims.

BRIEF DESCRIPTION OF DRAWINGS

These and other features, aspects and advantages of the present invention will become better understood with reference to the accompanying drawings, wherein:

FIG. 3 is a front view of FIG. 2;

FIG. 4 is a side view of FIG. 2;

FIGS. 8 and 8A are each a front view and a top view showing another embodiment of the present invention wherein the;

DETAILED DESCRIPTION OF THE PREFERRED EMBODIMENTS

Figure 1:
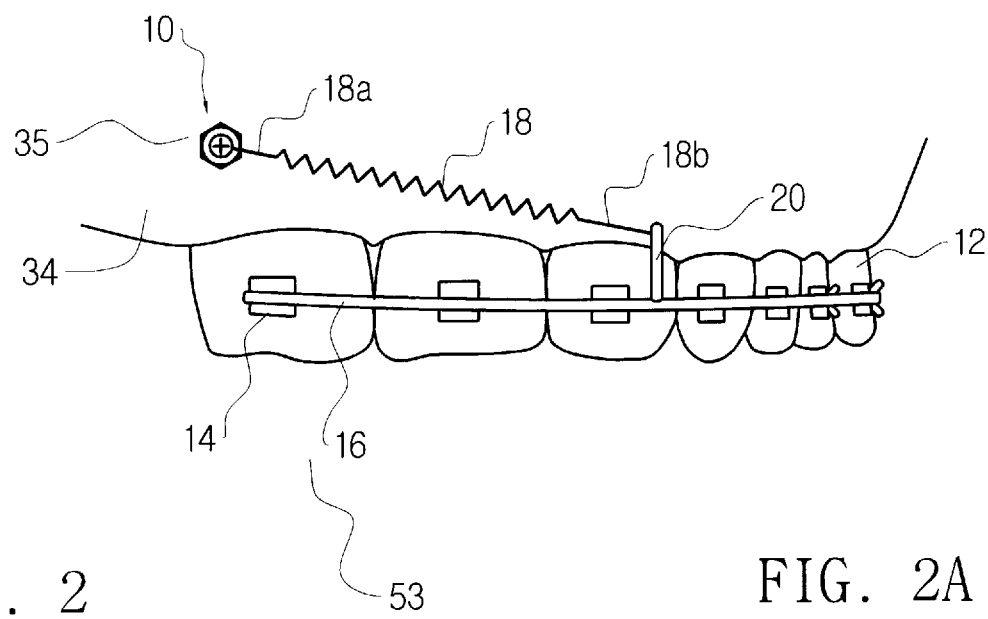
FIG. 1 is a view showing an osteogenic support device for an orthodontic treatment applied on an orthodontic patient according to the present invention.
Figure 2:
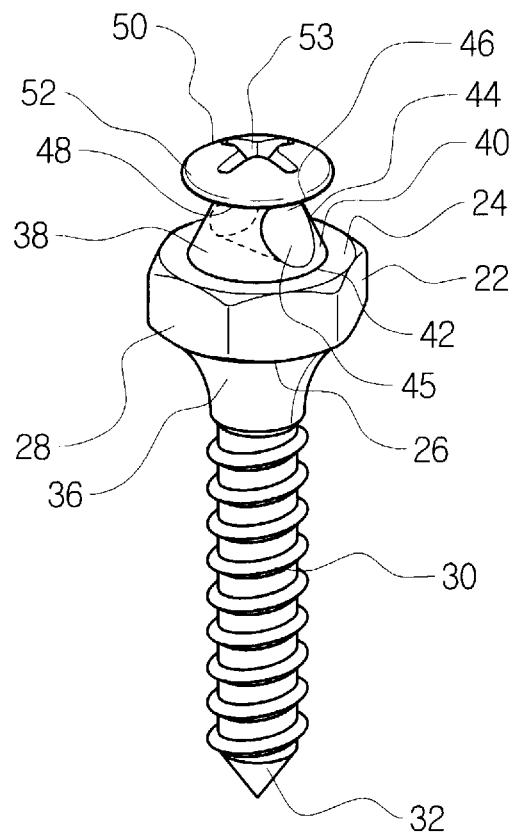
FIG. 2 is a perspective view showing an osteogenic support device for an orthodontic treatment according to the present invention.
Figure 2A:
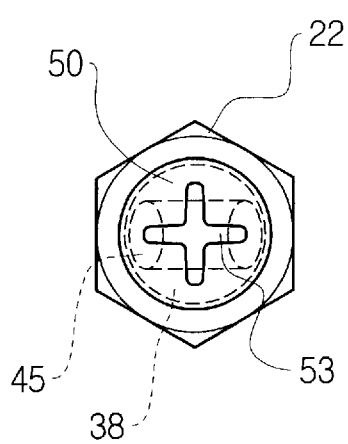
FIG. 2A is a top view of FIG. 2.

As shown in FIG. 1, an osteogenic support device 10 for an orthodontic treatment according to the present invention is used to provide an extra force to teeth 12 of an orthodontic patient. As shown therein, brackets 14 are detachably glued on each outer surface of the teeth 12 and a base wire 16 is aligned along the brackets 14 to become attached to the brackets 14 so as to generate strain for teeth realignment. When the base wire 16 is not sufficient to generate teeth correction, an osteogenic support device 10 is selectively utilized in conjunction with the base wire 16.

The osteogenic support device 10 is partially planted in upper or lower jaw bone during the orthodontic treatment and linked by an elastic member 18 to the base wire 16. Specifically, the elastic member 18 is connected to the osteogenic support device 10 by first end 18a and to the base wire 16 by second end 18b thereof. Alternately, a wire support 20 may be provided between the second end 18b of the elastic member 18 and the base wire 16 to improve treatment efficiency. The wire support 20 is formed in a sustainable material and adjustably engaged by its one end to the base wire 16 while the other end thereof is hooked by the elastic member 18 such that the overall connection between the osteogenic support device 10 and the base wire 16 can be further controlled to a precise extent required while protecting gum 35 depending upon orthodontic patients.

In a preferred version, the elastic member 18 may be one selected from an elastically processed wire, a plastic string, a fabric string and other string type connection materials. The wire support 20 may be formed of a solid material and processed to meet individual requirements depending upon teeth-to-gum curves and shapes.

With reference to FIGS. 2, 2A, 3 and 4, the osteogenic support device 10 for an orthodontic treatment includes a platform 22 defined by a top side 24, a bottom side 26 and an outer periphery 28. Extended from the bottom side 26 of the platform 22 is a lower projection 30 that has a pointed end 32 so as for the lower projection 30 to become pierced in an osteogenic jaw bone structure 34 of an orthodontic patient for a limited time period. The lower projection 30 is substantially threaded to facilitate its planting in the osteogenic jaw bone structure 34. Also, it is preferred that the lower projection 30 ranges between about 5.0 mm and 8.0 mm in length.

Between the platform 22 and the lower projection 30 is also provided a gum protection 36 to guard a gum portion 35 of the osteogenic jaw bone structure 34. The gum protection 36 is smoothly tapered from below the platform 22 toward the lower projection 30. The tapering of the gum protection 36 may be implemented either in a proportional decrement like a side line of a cone or in an inwardly exponential decrement like a side line of a bottle neck. Here, the inwardly exponential decrement is substantially preferred in formation of the gum protection 36. The height of the gum protection 36 is preferably formed between about 1.0 mm to 5.0 mm depending on orthodontic patients.

The osteogenic support device 10 further comprises an upper projection 38 that is provided to upwardly extend from the top side 24 of the platform 22. The upper projection 38 includes a base portion 40 having a lower end 42, a mid portion 44, and an upper portion 46 having an upper end 48. The lower end 42 of the base portion 40 of the upper projection 38 is attached to the top side 24 of the platform 22. Here, the upper projection 38 is substantially tapered from the base portion 40 toward the upper portion 46 thereof so that the elastic member 18 when hooked up over the upper projection 38 can be placed as much distanced from the platform 22 as possible.

In a preferred embodiment, the mid portion 44 of the upper protection 38 has a through opening 45 whose axis is substantially perpendicular to an axis of the lower projection 30 so that a safe hookup of the first end 18a of the elastic member 18 becomes realized via the through opening 45. The through opening 45 is preferably formed in a cylindrical shape to facilitate an intake and subsequent hookup of the first end 18a of the elastic member 18 around the upper projection 38.

In order to protect an oral skin portion (not shown) of an orthodontic patient that may become in contact with the osteogenic support device 10 during the orthodontic treatment period, a cap 50 is formed to cover over the upper end 48 of the upper portion 46 of the upper projection 38. The cap 50 is defined by an upper surface 52 and a lower surface 54 so the upper end 48 of the upper portion 46 of the upper projection 38 is attached to the lower surface 54 of the cap 50. The lower surface 54 of the cap 50 is substantially larger in area than the upper end 48 of the upper portion 46 of the upper projection 38 to provide a reliable accommodation of the first end 18a of the elastic member 18 between the cap 50 and the platform 22.

The upper surface 52 of the cap 50 is shaped in dome, and the domed upper surface 52 of the cap 50 is partially depressed to form a recess 53 either in a linear formation or in a cross-shaped formation. Selectively, the upper surface 52 of the cap 50 may be scratch-processed to harmonize with the oral skin portion contacted therewith without producing negative side effects.

Meanwhile, it is recommended that the lower end 42 of the lower portion 40 of the upper protection 38 is equal to or less than the top end 24 of the platform 22 in area. The upper projection 38 is shaped in a truncated cone, and the truncated cone shaped upper projection 38 is between about 1.0 mm and about 3.0 mm in height.

Figure 5:
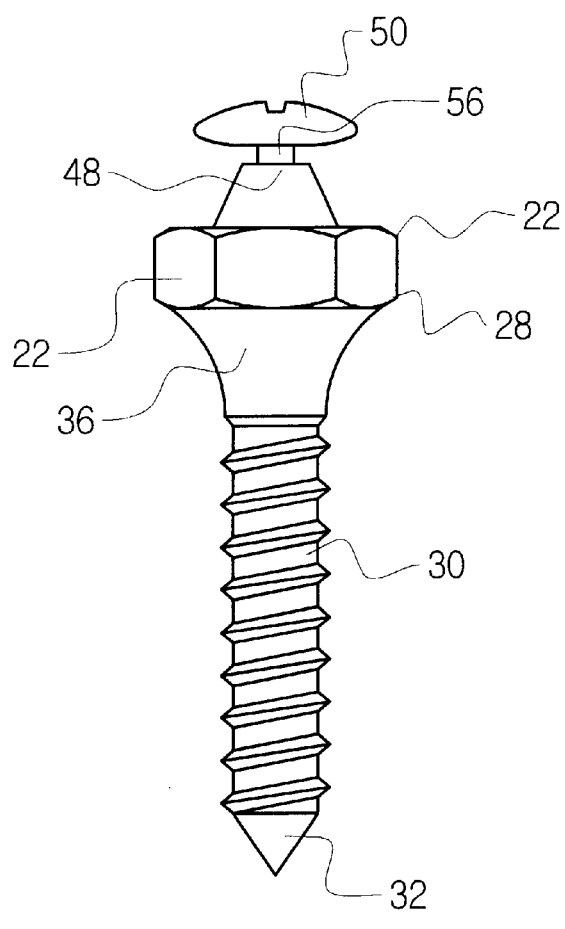
FIGS. 5 and 6 are views each showing an osteogenic support device for an orthodontic treatment according to embodiments of the present invention.
Figure 6:
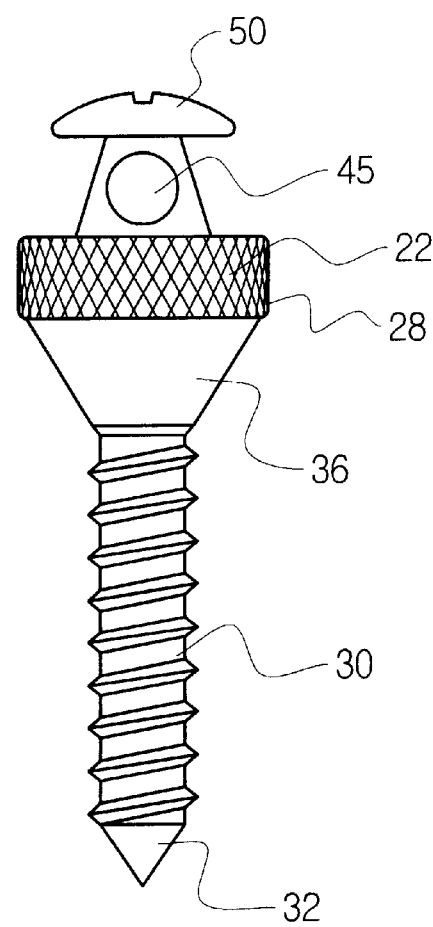
Figure 7:
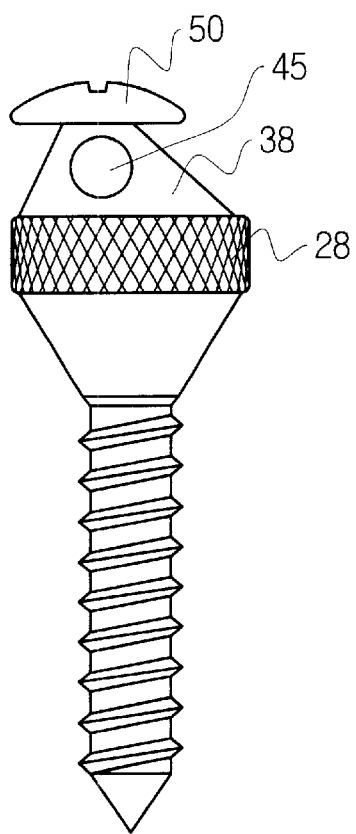
FIGS. 7 and 7A are each a front view and a top view showing another embodiment of the present invention wherein the upper projection is formed eccentric.
Figure 8:
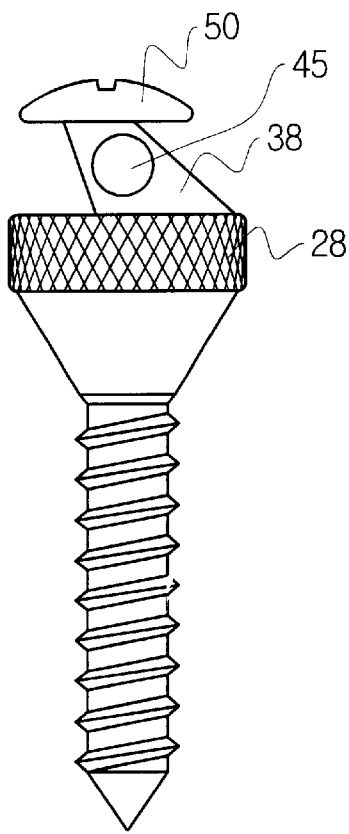
Figure 9:
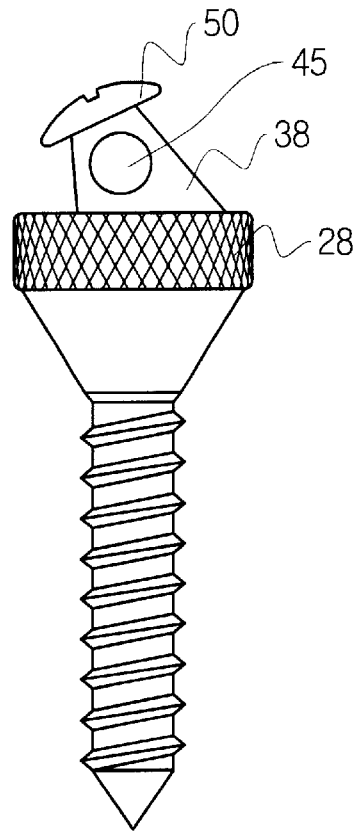
FIGS. 9 and 9A are each a front view and a top view showing another embodiment of the present invention.
Figure 7A:
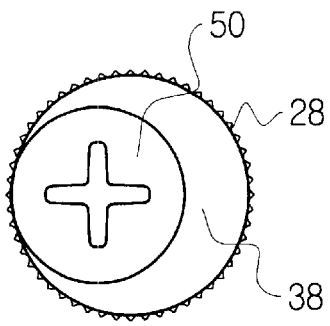
Figure 8A:
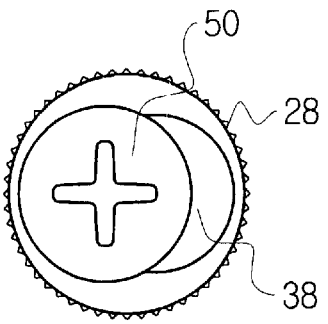
Figure 9A:
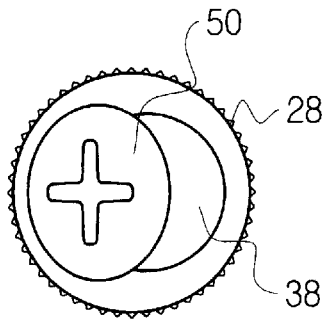
Figure 10:
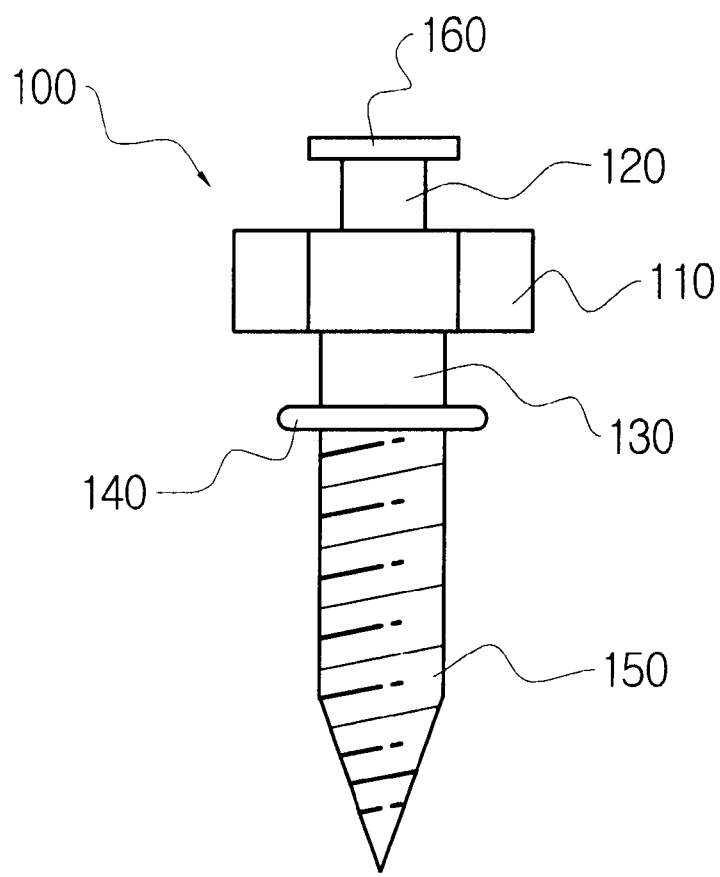
FIG. 10 is a view showing a conventional osteogenic screw.

As shown in FIGS. 5 and 6, the outer periphery 28 of the platform 22 is formed in a multi-sided alignment. For example, the outer periphery 28 of the platform 22 may be formed in a six-sided peripheral alignment to facilitate the partial planting of the osteogenic support device 10 in a target portion of the orthodontic patient's jaw bone structure 34. Selectively, the outer periphery 28 of the platform 22 may be substantially surface-piled to facilitate manipulation of the support device 10 to plant the lower projection 30 in the jaw bone structure 34 and remove the planting after completion of the orthodontic treatment.

In the construction as described above, the lower projection 30 is planted in the jaw bone structure of an orthodontic patient, and the first end 18*a* of the elastic member 18 is hooked between the cap 50 and the platform 22 while the second end 18*b* of the elastic wire 18 is hooked up either with the base wire 16 which links each bracket 14 attached on teeth 12 or with the wire support 20 that is connected to the base wire 16 in a substantially vertical alignment. Also, when the through opening 45 is formed through the mid portion 44 of the upper projection 38, the first end 18*a* of the elastic member 18 may pass through the through opening 45 and become surrounded over between the cap 50 and the platform 22 so as to provide a firm engagement of the elastic member 18 to the upper projection 38.

In another embodiment as further shown in FIG. 5, a cylindrical bar extension 56 is provided between the lower surface 54 of the cap 50 and the upper end 48 of the upper portion 46 of the upper projection 38. Here, the area on the upper end 48 of the upper portion 46 of the upper projection 38 is larger than the area on each axial end surface of the cylindrical bar extension 56 so as to easily guide the hookup of the elastic member 18 around the upper projection 38 to the lower surface 54 of the cap 50. In order to derive a desired outcome, it is preferred that the bar extension 56 is less than one third of the upper projection 38 in height.

As shown in FIGS. 7–7A, 8–8A, and 9–9A, the upper projection 38 may vary in formation depending upon an angle made by the elastic member 18 and the planted lower projection 30. That is, since different osteogenic jaw bone structures 34 lead to angular differences in planting, the formation of the upper projection 38 needs to vary in formation so as to optimize control of teeth alignment correction. Accordingly, the upper projection 38 may be formed substantially eccentric from the axis of the lower projection 30. Namely, the upper projection 38 may become eccentric so that an angle formed by each axis of the upper projection 38 and the lower projection 30 may range between about 20 degrees and 70 degrees.

An advantage of the osteogenic support device for an orthodontic treatment according to the present invention is that the upper projection 38 tapered toward the cap 50 at least decreases or eliminates possibility that the elastic wire 18 hooked over the cap by one end 18*a* and the base wire 16 linking each bracket 14 glued on target by the other end 18*b* may become in contact with gum 35, thereby preventing gum inflammation and other friction related gum diseases since the tapered upper projection 38 serves to distance the elastic wire 18 from the gum 35.

In addition, the tapered upper projection 38 stabilizes placement of the elastic wire 18 while preventing unwanted drooping and swaying of the elastic wire 18, thereby improving efficiency of the orthodontic treatment and decreasing an overall time period during which the lower projection stays pierced in the osteogenic jaw bone structure 34. Moreover, the gum protection 36 formed in taper from the platform 22 toward the lower projection 30 is provided such that it minimizes gum stimulation and gum contact area while staying contacted with the gum, thereby overcoming disadvantages by a conventional disk-typed gum contact that disregards pressure on the gum 35.

Although the invention has been described in considerable detail with reference to certain preferred versions thereof, other versions are possible by converting the aforementioned construction. Therefore, the scope of the invention shall not be limited by the specification detailed above and the appended claims.

What is claimed is:

1. An osteogenic support device for an orthodontic treatment, comprising:
   a) a platform defined by a top side, a bottom side and an outer periphery, wherein a lower projection having a pointed end extends from the bottom side of the platform so as to become pierced in an osteogenic jaw bone structure of an orthodontic patient for a limited time period;
   b) an upper projection upwardly extending from the top side of the platform, wherein the upper projection includes a base portion having a lower end, a mid portion, and an upper portion having an upper end, wherein the lower end of the base portion of the upper projection is attached to the top side of the platform, wherein the upper projection is substantially tapered from the base portion toward the upper portion thereof; and
   c) a cap having an upper surface and a lower surface, wherein the upper end of the upper portion of the upper projection is attached to the lower surface of the cap, wherein the lower surface of the cap is substantially larger in area than the upper end of the upper portion of the upper projection.

2. The osteogenic support device of claim 1 further comprising an elastic wire having first and second ends, wherein the first end of the elastic wire is hooked between the cap and the platform, wherein the second end of the elastic wire is hooked with an orthodontic wire which links each bracket attached on teeth of the orthodontic patient.

3. The osteogenic support device of claim 1 further comprising a gum protection between the platform and the lower projection, wherein the gum protection is smoothly tapered from below the platform toward the lower projection.

4. The osteogenic support device of claim 1 wherein the upper projection is shaped in a truncated cone.

5. The osteogenic support device of claim 4 wherein the truncated cone shaped upper projection is between about 1.0 mm and about 3.0 mm in height.

6. The osteogenic support device of claim 1 wherein the lower projection is substantially threaded.

7. The osteogenic support device of claim 1 wherein the outer periphery of the platform is substantially surface-piled to facilitate manipulation of the support device.

8. The osteogenic support device of claim 1 wherein the upper surface of the cap is shaped in dome.

9. The osteogenic support device of claim 8 wherein the domed upper surface of the cap is partially depressed to form either a linear recess or a cross-shaped recess.

10. An osteogenic support device for an orthodontic treatment, comprising:
   a) a platform defined by a top side, a bottom side and an outer periphery, wherein a lower projection having a pointed end extends from the bottom side of the platform so as to become pierced in an osteogenic jaw bone structure of an orthodontic patient for a limited time period;

b) an upper projection upwardly extending from the top side of the platform, wherein the upper projection includes a base portion having a lower end, a mid portion, and an upper portion having an upper end, wherein the lower end of the base portion of the upper projection is attached to the top side of the platform, wherein the upper projection is substantially tapered from the base portion toward the upper portion thereof, wherein the mid portion of the upper protection has a through opening substantially perpendicular to an axis of the lower projection; and c) a cap having an upper surface and a lower surface, wherein the upper end of the upper portion of the upper projection is attached to the lower surface of the cap, wherein the lower surface of the cap is substantially larger in area than the upper end of the upper portion of the upper projection.

11. The osteogenic support device of claim 10 further comprising an elastic wire having first and second ends, wherein the first end of the elastic wire is hooked between the cap and the platform, wherein the second end of the elastic wire is hooked with an orthodontic wire which links each bracket attached on teeth of the orthodontic patient.

12. The osteogenic support device of claim 10 further comprising a gum protection between the platform and the lower projection, wherein the gum protection is smoothly tapered from below the platform toward the lower projection.

13. The osteogenic support device of claim 10 wherein the lower projection is substantially threaded.

14. The osteogenic support device of claim 10 wherein the outer periphery of the platform is substantially surface-piled to facilitate manipulation of the support device.

15. The osteogenic support device of claim 10 wherein the upper surface of the cap is shaped in dome.

16. The osteogenic support device of claim 15 wherein the domed upper surface of the cap is partially depressed to form either a linear recess or a cross-shaped recess.

* * * * *